United States Patent [19]

Moro et al.

[11] 4,265,620

[45] May 5, 1981

[54] SYSTEM FOR SIMULATING THE CONDYLE MOVEMENTS

[76] Inventors: Gianni Moro, Viale Nazario Sauro 81; Mario Picchi, Corso Mazzini 18, both of Leghorn, Italy

[21] Appl. No.: 62,330

[22] Filed: Jul. 31, 1979

[30] Foreign Application Priority Data

Aug. 8, 1978 [IT] Italy .................................. 9556 A/78

[51] Int. Cl.³ .............................................. A61C 19/04
[52] U.S. Cl. ........................................ 433/69; 433/54
[58] Field of Search ............................ 433/69, 68, 54; 128/777

[56] References Cited

U.S. PATENT DOCUMENTS

| | | | |
|---|---|---|---|
| 2,032,833 | 3/1936 | Broadbent | 433/68 |
| 2,119,824 | 6/1938 | Miller et al. | 433/54 |
| 2,829,435 | 4/1958 | Kazis et al. | 433/69 |
| 3,074,166 | 1/1963 | Skallerup | 433/69 |
| 3,130,494 | 4/1964 | MacKay | 433/69 |
| 3,822,694 | 7/1974 | Mills | 433/69 |
| 4,034,474 | 7/1977 | Lee | 433/69 |
| 4,197,855 | 4/1980 | Lewin | 128/777 |

*Primary Examiner*—Gene Mancene
*Assistant Examiner*—John J. Wilson
*Attorney, Agent, or Firm*—Hopgood, Calimafde, Kalil, Blaustein & Lieberman

[57] ABSTRACT

A system for simulating the condyle movements, for use in forming dental protheses, comprises a sensing apparatus including structures engageable with the cranium and mandible arch, and a reproducing apparatus which repeats the mastication movements sensed by sensing apparatus. The mastication movements are sensed by inductive sensors mounted on the sensing apparatus.

6 Claims, 28 Drawing Figures

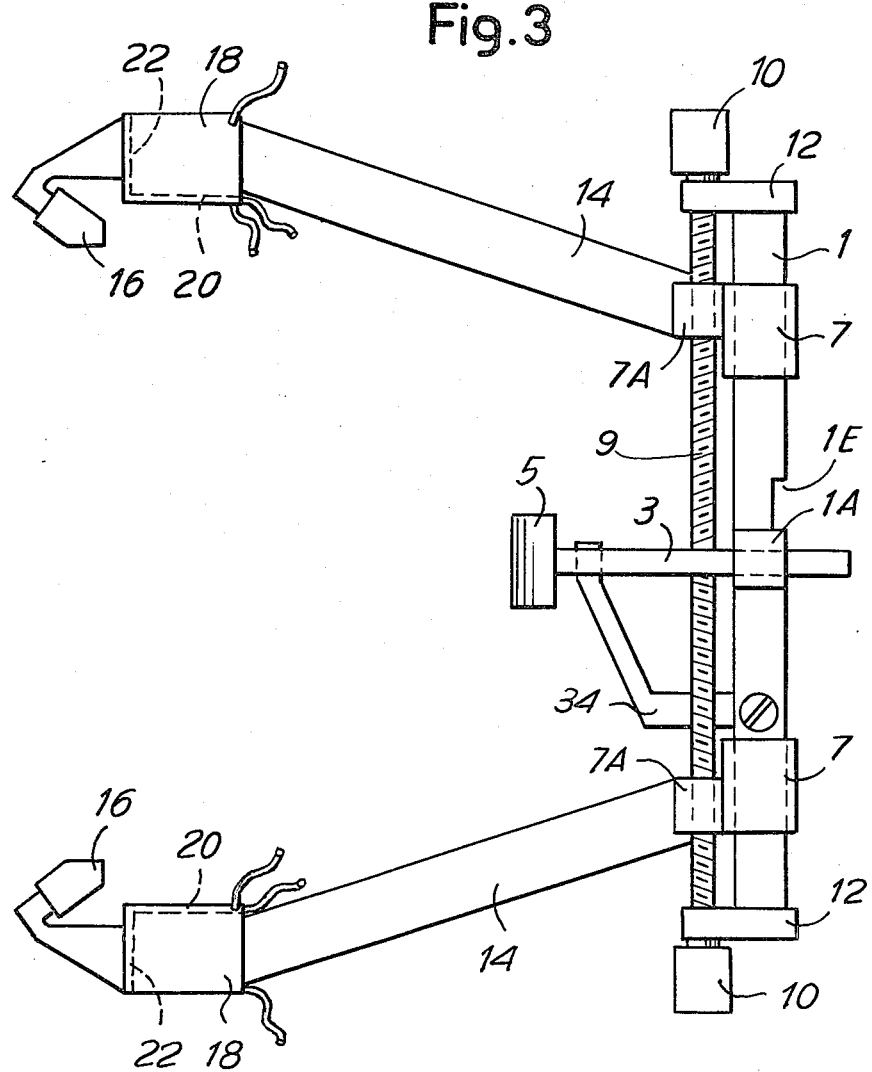

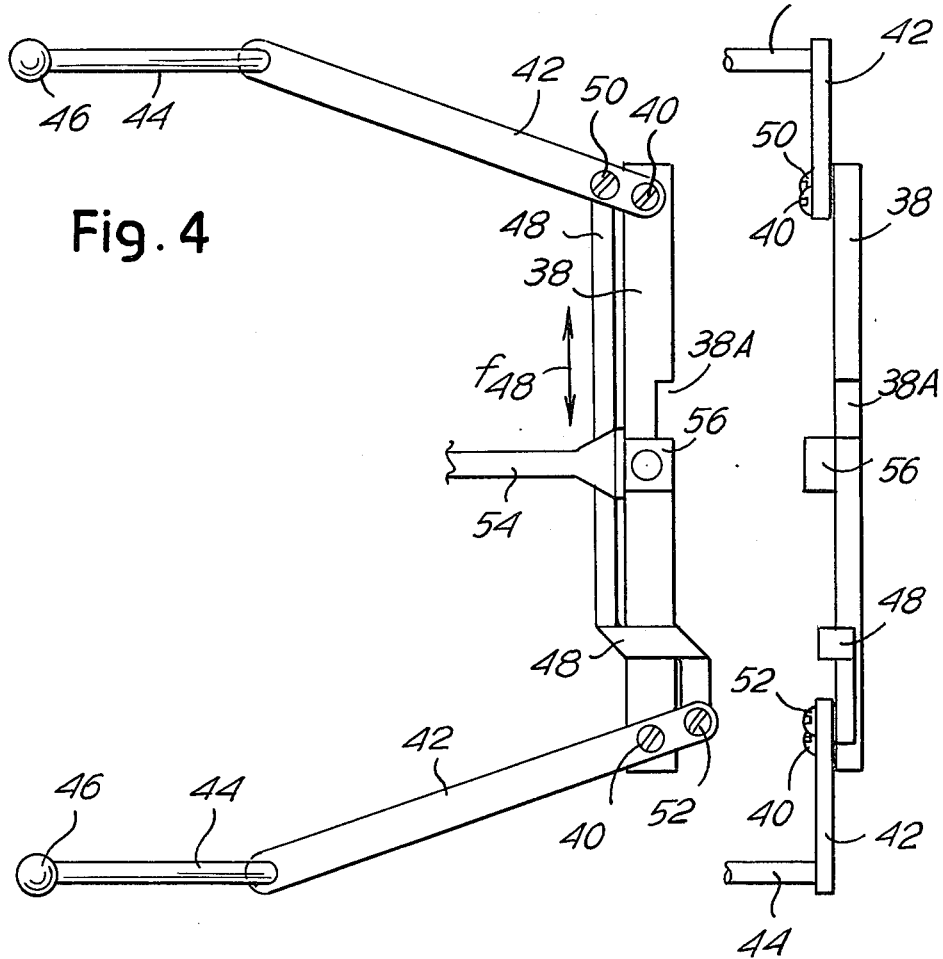

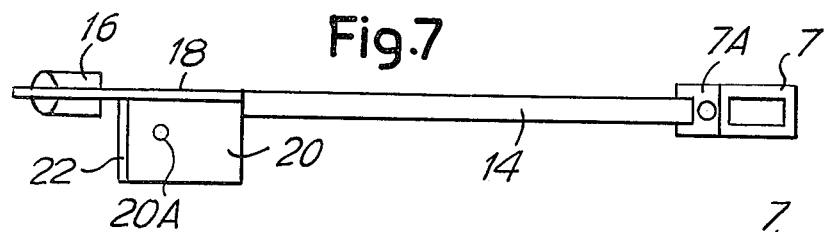
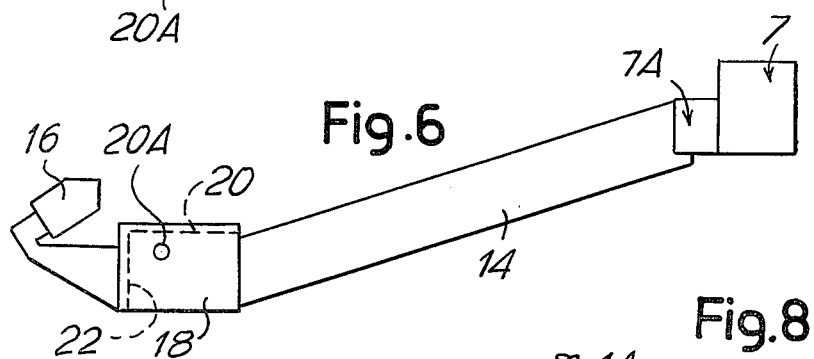
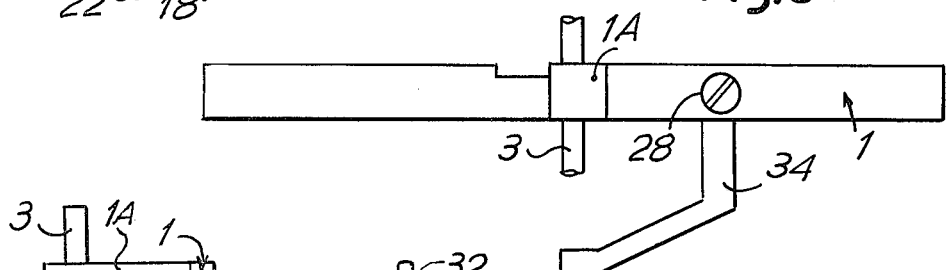
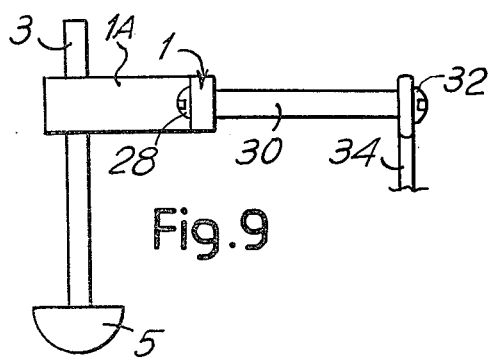
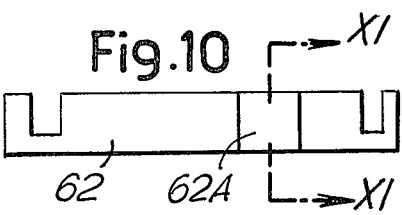
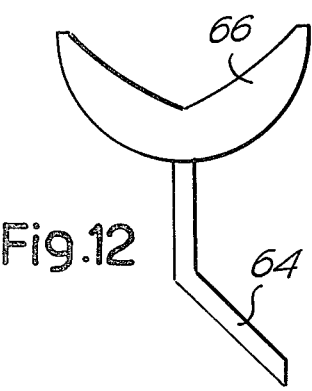
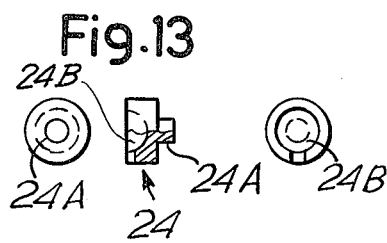

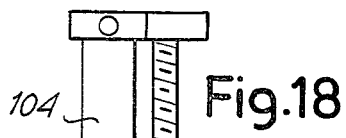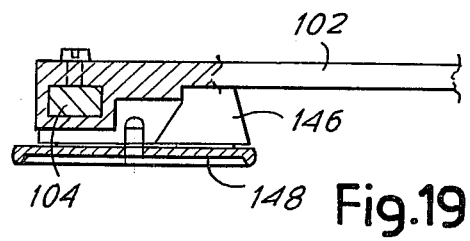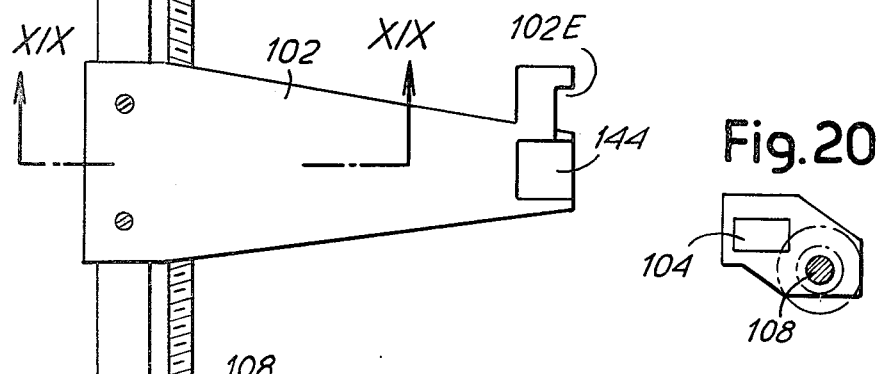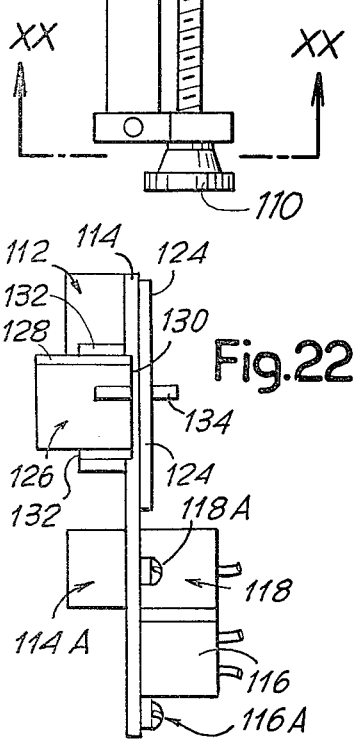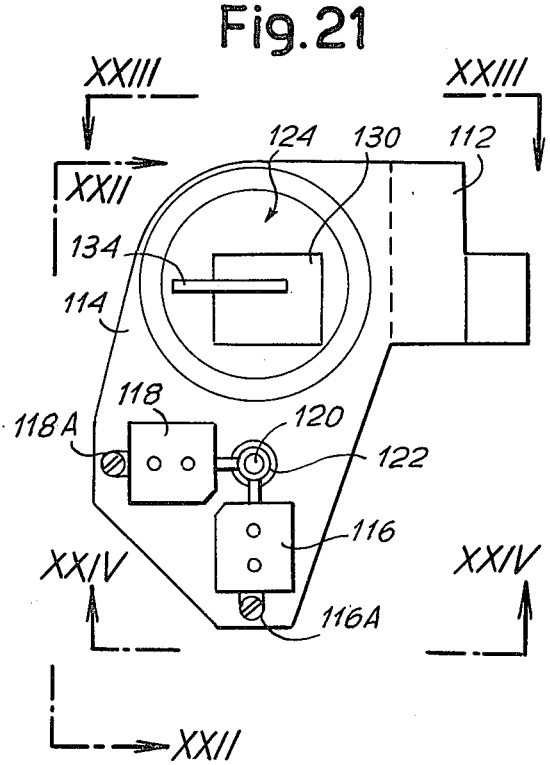

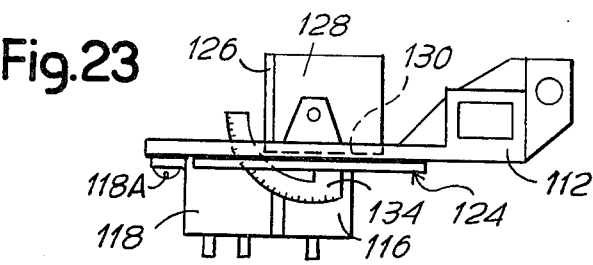
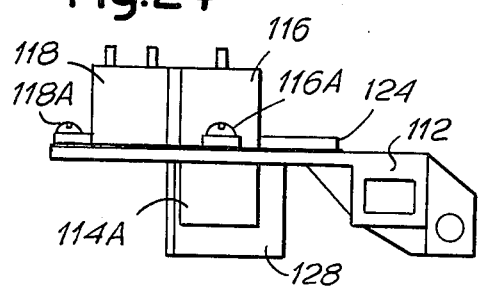
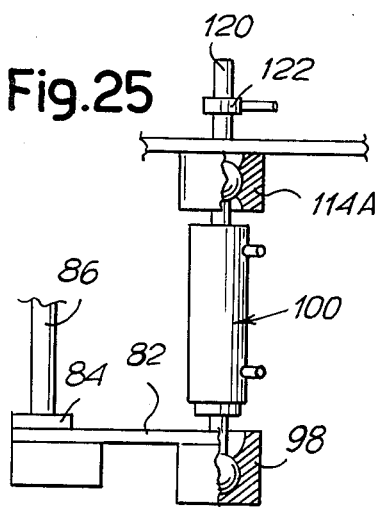
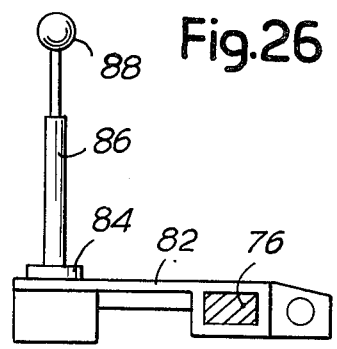
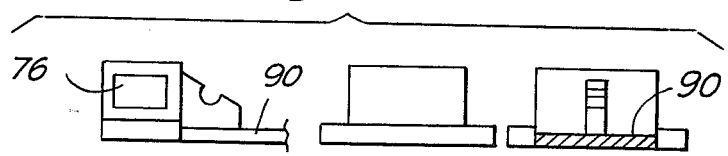

4,265,620

SYSTEM FOR SIMULATING THE CONDYLE MOVEMENTS

FIELD OF THE INVENTION

This invention relates to a system for simulating the condyle movements, that is the relative movements between the maxillary arch and the mandible arch, for forming dental protheses.

SUMMARY OF THE INVENTION

According to the present invention, there is provided a system for simulating the condyle movements, comprising a sensing apparatus and a reproducing apparatus which imposes the mastication movements on two arch moulds as determined by the sensing apparatus, wherein: said sensing apparatus comprises a structure for fitting to the cranium and thereby to the maxillary arch, a structure engageable with the mandible arch, means for generating a signal representing the relative distance between points of the two structures and the front of the arches, at a distance from the condyles, and two induction means each disposed adjacent to a respective one of the two condyles, each induction means comprising a group of three flat mutually perpendicular reference electrodes mounted on one of the structures, and a ball mounted on the other structure and cooperating with the electrodes in such a manner that a set of three relative positioning signals is generated by induction between the ball and the individual electrodes during the relative free movements; and said reproducing apparatus comprises two structures movable relative to each other, a base supporting one of said structures, and three extendable articulated members supporting the other of said structures, two of said members each having an end displaceable in two directions under the control of two of the signals of the two sets of three signals, the third signals controlling the extension of said members.

BRIEF DESCRIPTION OF THE DRAWINGS

An embodiment of the invention will now be described, by way of example only, with reference to the accompanying diagramatic drawings, in which:

FIG. 3 is a plan view on line III—III of FIG. 2;

FIGS. 4 to 13 show details of the apparatus of FIGS. 1 to 3;

FIGS. 17 and 18 are plan views respectively showing a lower fixed structure and an upper movable structure of the reproducing apparatus;

FIGS. 19 and 20 are sections respectively taken on lines XIX—XIX and XX—XX of FIG. 18;

FIG. 21 shows a detail of FIG. 16;

FIGS. 22, 23 and 24 are respectively part sectional views on line XXII—XXII, XXIII—XXIII and XXIV—XXIV of FIG. 21;

FIGS. 25 and 26 are respectively detailed sections on lines XXV—XXV and XXVI—XXVI of FIG. 17;

FIGS. 27 and 28 show further details of the lower structure.

DESCRIPTION OF THE PREFERRED EMBODIMENT

Figure 1:
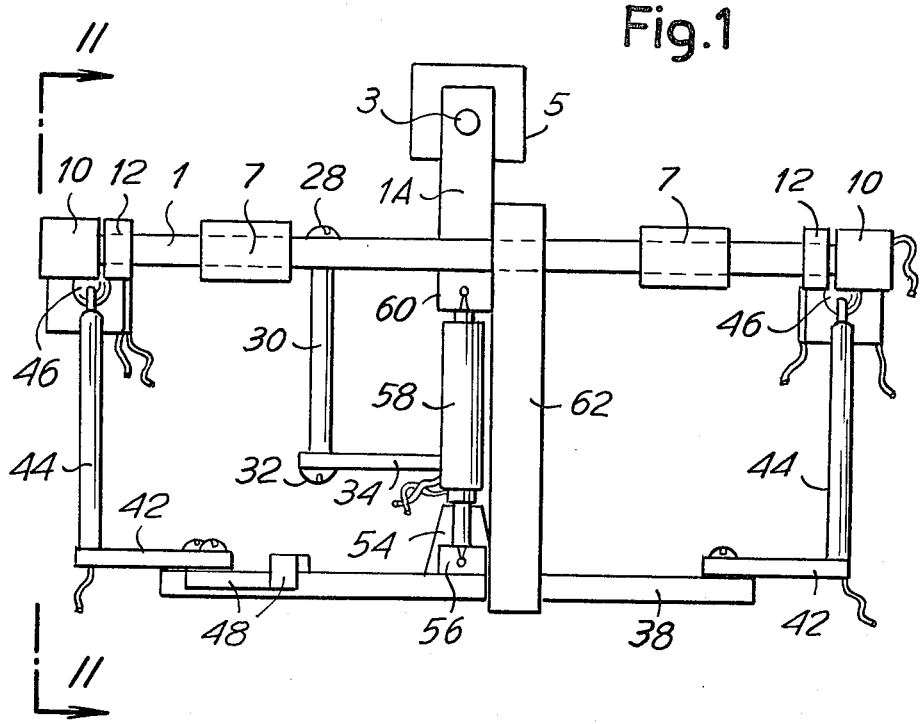
FIG. 1 is a front view of sensing apparatus for fitting to the patient's head.
Figure 2:
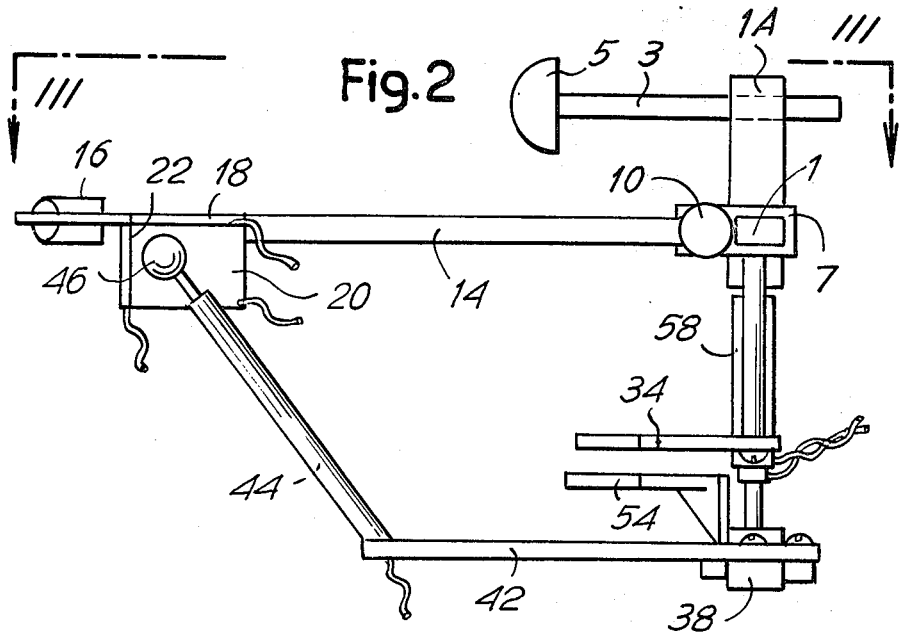
FIG. 2 is a side view on line II—II of FIG. 1.

FIGS. 1 to 13 show overall views and specific details of a pantographic sensing apparatus which is fitted to the patient in order to generate data and signals relative to the movements made by the teeth, i.e. the condyle movements, for the purpose indicated.

The apparatus comprises an upper structure for fitting to the cranium and consequently to the maxillary arch, and a lower structure for engaging with the mandible arch, these following the relative movements of the two arches.

The upper structure comprises a transverse slide guide 1 with a central column 1A for a support stem 3 which with a terminal 5 forms a contact reference device for the glabella, the stem 3 being adjustable. Two symmetrical slides 7 are adjustable on the slide guide 1, and can be made to approach or withdraw from each other symmetrically by means of a micrometer screw 9 with two opposing threads controlled by knobs 10, the screw 9 being supported by lateral supports 12 on the guide 1 and being engaged in seats 7A in the slides 7. Two arms 14 are rigid with the slides 7, and extend with a slight divergence from each other to support at their distal ends signals generating means for fitting to the cranium structure at the ears. The arms 14 terminate in ear pieces 16 engageable in the auricular canals.

At the condyle, each arm 14 comprises three mutually perpendicular flat reference elements constituting induction electrodes, and comprising an upper horizontal electrode 18, a middle electrode 20 and a front-rear electrode 22. The plates of the middle electrodes 20 each comprise a seat in the form of a bore 20a for receiving the shank 24A of a gauging member 24 (see FIG. 13) for positioning a member cooperating with the flat electrodes 18,20,22. This latter member is constituted by a ball 46 (to be described hereinafter) which can be received in a recess 24B in the respective gauging member 24. The gauging members 24 are removed from the bores 20a after centering, i.e. after lateral zeroing.

A downwardly extending column 30 is rigidly connected by screw means 28 to the guide 1, and carries, rigidly connected thereto by a screw 32, a support 34 for a maxillary reference device to which is fitted a temporary prothesis designed for fixing to the upper maxilla.

The described upper structure can therefore be rigidly fitted to the maxilla and cranium by means of the ear pieces 16 which can be moved towards each other by the screw 9, and by the supports 5 and 34, and thus participates in the movements thereof.

A lower structure, which has to participate in the movements of the mandible, comprises a support crosspiece 38 to which two arms 42 are hinged at 40. By means of telescopically extendable struts 44, the arms 42 support the balls 46 which cooperate with the two groups of electrodes 18,20,22.

The balls 46—which are supported at the ends of the telescopically extendable struts 44—are each positioned relative to the respective electrodes by means of the gauging members 24. For this purpose, the arms 42 can be move simultaneously and symmetrically, in order to cause the balls 46 to approach and withdraw from each other, by means of a bar 48 hinged at 50 to one of the arms 42 and at 52 to the other arm 42. The hinges 50 and 52 lie on opposite sides of the associated hinges 40, so that on moving the bar 48 as indicated by double arrow f48 in one direction, the balls 46 move away from each other and in the other direction they aproach each other, so that they can be brought near to, and centred, i.e. zeroed (by means of the gauges 24) with respect to the electrodes 18,20,22.

A support 54 is fixed to the crosspiece 38 to serve as a mandible reference device i.e. for rigidly connecting the lower structure 46,44,42,38 to the mandible—by means of a temporary prothesis—in order to follow its movements.

The crosspiece 38 comprises an articulated support 56 for a ball joint to which a telescopic sensor 58 is connected, the sensor 58 comprising a capacitive coupling cylinder between the ball joint engaged with the support 56 and a similar ball joint engaged with the guide 1. By means of the coupling cylinder, a signal is obtained depending on the relative movements of the front parts of the maxillary and mandible arches, which determines the "rotation" which the balls undergo as the arches are opened and closed.

Electrical connections are made between each ball 46 and each of the electrodes 18,20, and 22 by ways of measuring circuits and instruments, so as to obtain continuously variable signals which depend on the relative approach and withdrawal movements between the ball and each electrode. Consequently, during mastication, three continuously variable signals are obtained for each ball, which instantaneously supply the three position coordinates of the ball relative to the electrodes 18,20,22 with which they are coordinated, and relative to which an initial, i.e. zero position, for the ball 46 is given by the gauge 24 which is subsequently removed. The angular movement of the balls is determined by the continuous measurement obtained with the front capacitive coupling cylinder, i.e. the sensor 58, which generates continuous signals for evaluating the relative withdrawal and approach of the joints on the supports 60 and 56.

On fitting the apparatus, the upper and lower structures are connected together by a bracket 62 which engages in seats 38A and 1E formed in the members 38 and 1 (see also FIGS. 10 and 11). An arm 64 supporting an anatomical occlusal reference fork 66 can be connected to the bracket 62 in a bevelled seat 62A. The purpose of this fork is to take the upper and lower impressions of the patient and enable the patient's moulds to be spacially positioned in the reproduction apparatus for the mastication movements in the subsequent processing.

The pantograph sensing apparatus, which is constructed of materials such as to provide a low weight structure, is fitted to the patient by means of the ear pieces, the supports 5 and 34, and the support 54, while maintaining the upper and lower structures connected together by the bracket 62, and keeping the balls 46 centred by the gauges 24. After fitting, the gauges 24 are removed, as is the bracket 62 (with which the impressions have been previously taken by means of the fork 66). The upper and lower structures of the apparatus are thus released from each other. The upper structure is rigid with the cranium and the maxillary arch by way of the joint of the support 60 and the electrodes 18,20,22. The lower structure is rigid with the mandible arch by way of the joint of the support 56 and the balls 46. Mastication can take place freely, as the two balls are completely free to repeat the movements of the condyle relative to the perpendicular electrodes 18,20,22, and as the constraint formed by the sensor 58 is very loose due to the ease of sliding of the capacitive coupling cylinder and the agility of the end joints. The mastication movements therefore take place practically without alteration, and are continuously determinable by the signals obtained by the action between the two balls and each of the associated electrodes, and by the relative sliding movements in the sensor 58.

Figure 14:
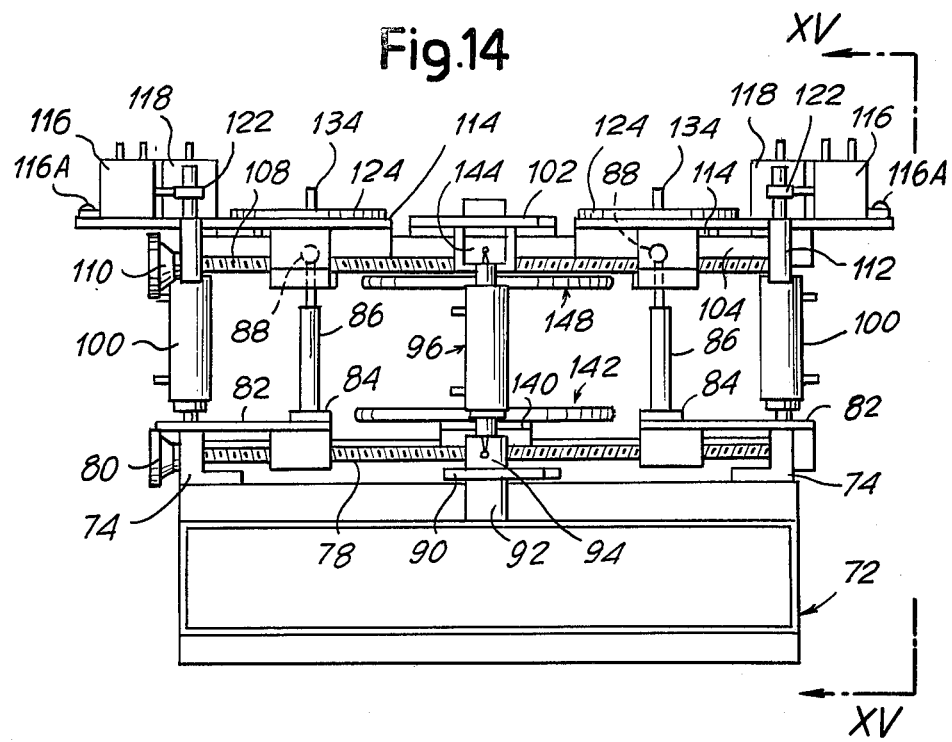
FIGS. 14, 15 and 16 are a front view, a side view on line XV—XV of FIG. 14, and a plan view respectively, of a reproducing apparatus.
Figure 15:
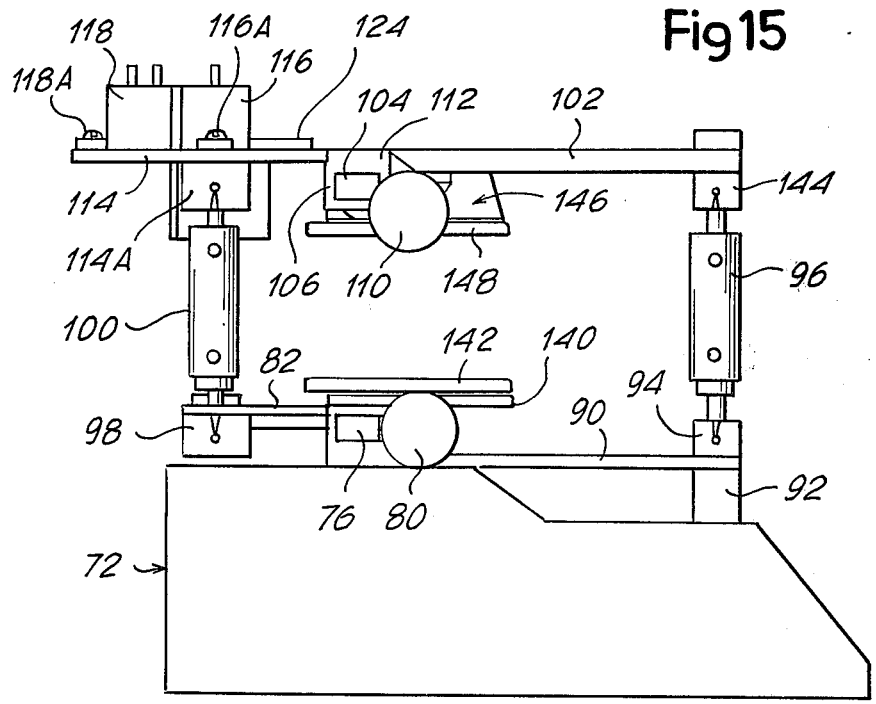
Figure 16:
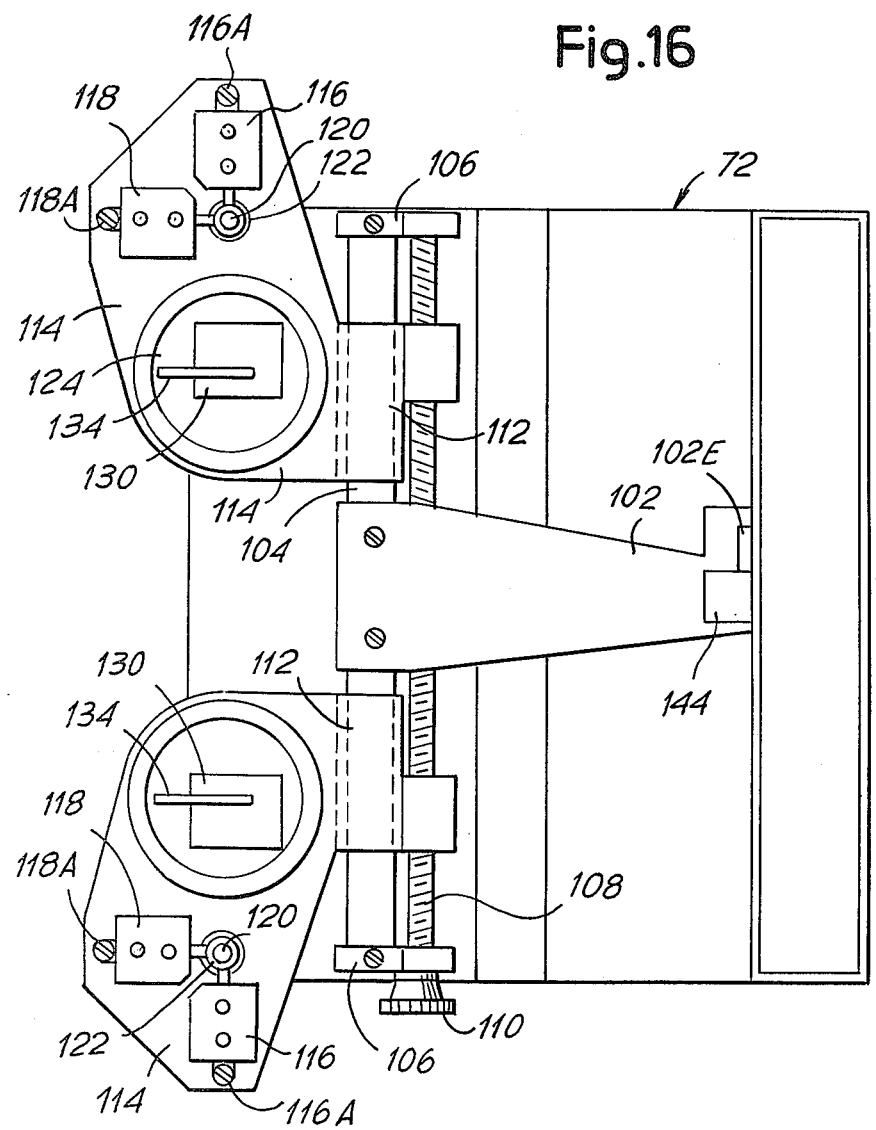
Figure 17:
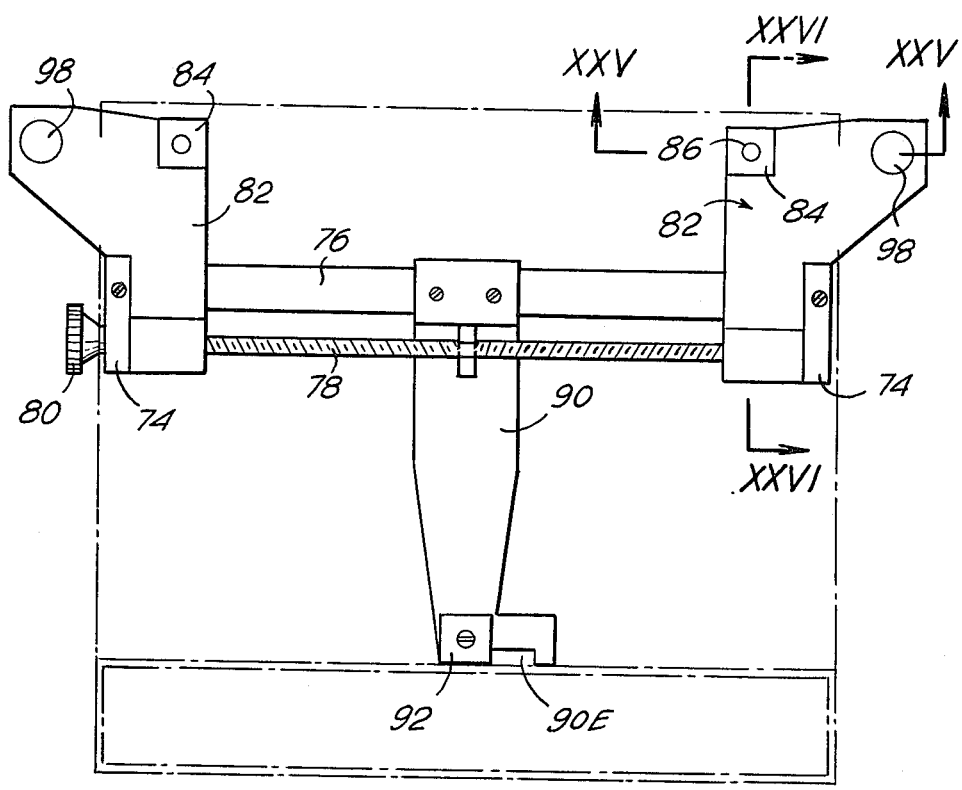

FIGS. 14 and 28 show the reproducing apparatus, to which signals provided (either directly or after recording) by the pantographic sensing apparatus are fed in order to repeat the mastication movements on the mould.

The reproducing apparatus comprises a base 72 having supports 74 on which are mounted a slide guide 76 and a micrometer screw 78 with opposing threads and operable by a knob 80. In this manner, two supports 82 can be adjusted symmetrically by sliding. Vertical telescopically adjustable columns 86 are mounted on these supports by way of bases 84 and carry two balls 88 (see FIG. 26 in particular) which reproduce the spacial positions of the balls 46. A lower support 90 is fixed centrally to the guide 76, and a column 92 to the base 72. In the column 92, a seat 94 forms an articulated joint for a servo-mechanism 100 for the vertical lateral movements. The two servo-mechanisms 100 are operated as a function of the signals generated in response to the vertical movements represented by the respective horizontal electrodes 18 and the respective balls 46. The two servo-mechanisms 100 are connected upperly to two perpendicular servo-mechanisms and controlled thereby, these imposing horizontal movements (looking at the drawing) on an upper structure to be described, this structure being movable relative to the base 72.

This upper structure comprises a support plate 102 fixed to an upper transverse guide 104 provided at its ends with supports 106 for a micrometer screw 108 with two opposing threads, and which is operable by a knob 110. Two symmetrical slides 112, each of which carries a support plate 114 for the condyle unit, are mounted on the two opposing symmetrical threads of the screw 108. Each assembly 112, 114 is supported symmetrically with respect to the other, so that they are spaced in the same relative manner as the two sets of electrodes 18,20,22. Two fluid servo-mechanisms 116 and 118 are mounted on each of the support plates 114. The first servo-mechanism repeats the mesiodistal displacements on the basis of the signals generated by the inductive effect between each respective ball 46 and its the associated electrodes 20. The second servo-mechanism 118 imposes front-rear displacements on the basis of the signals generated by the inductive effect between each respective ball 46 and its associated electrode 22. The two displacements are imposed on a single control rod 120 by way of a ring 122, the rod 120 being carried by the servo-mechanism 100. The servo-mechanism 100 can be extended and retracted to change the distance between the joint in the support 98 and an upper joint in a support 114A on the corresponding plate 114.

The rod 120 extends beyond the plate 114 and is connected in an inclinable manner to the ring 122. This ring is combined in an articulated manner with the movable elements of the two servo-mechanisms 116 and 118 to receive their combined movements, the two servo-mechanisms being pivoted at 116A and 118A so that their position can be varied in relation to the extension and retraction movements of the two servo-mechanisms and the orientation of the rod 120, which is determined by the combination of the movements due to the two servo-mechanisms 116 and 118. Each plate 114 comprises a large circular seat for a circular platform 124 which can be orientated in its own plane. Below the platform 124 there are two mutually perpendicular flat reference elements in the form of electrodes 126 and 128 which correspond to the electrodes 20 and 22, and cooperate with the ball 88 in a like manner to the cooperation between the electrodes 20 and 22 and the corresponding ball 46. The angular adjustment of the platform 124 in its plane is provided so as to introduce the so-called Bennet angle, i.e. a correction to obtain from the prothesis a corrective effect on the masticatory habits which may be found in the patient. A third flat electrode 130 which is perpendicular to the electrodes 126 and 128 carries these electrodes and is carried by a member oscillating about a pair of lugs 132 so as to orientate the electrode 130 to impose further corrections, which can be determined by a sector 134. The electrode 130 also cooperates with the ball 88, and carries the electrodes 126 and 128, displacing them relative to the platform 124. The electrodes 126, 128 and 130 define three reference planes.

The servo-mechanisms 100,116,118 are controlled by a differential effect, by comparing the signals obtained from the sensing apparatus of FIGS. 1 to 13 and the corresponding signals of the pairs of inductive sensors represented by the ball 88 and each of the electrodes 126,128, and 130.

By means of an intermediate member 140, the assembly 90 supports the disc 142 to which a lower mould is applied.

The support 102 is connected to the servo-mechanism 96 by way of a joint 144. The support 102 carries the upper disc 148 for an upper mould by way of an intermediate member 146.

The two supports 90 and 102 comprise seats 90E and 102E for receiving the bracket 62 with the fork 66 for initially positioning the impressions between the two support discs 142 and 148, which enables the moulds to be placed on the discs 142 and 148, in a manner which spacially corresponds to their determined spacial position, after which the bracket 62 and fork 66 with the impressions are removed, to leave the two moulds in a state in which they can cooperate in the relative movement imposed on them by the movement of the upper structure (comprising the elements 102,104,114 and the electrodes 126,128,130) relative to the lower structure (comprising the elements 90,76,82) which remains fixed to the base. The relative movements between the two structures are imposed by the servo-mechanism 96 (which repeats the movements of the sensor 58) and the two groups of three servo-mechanisms 100,116 and 118, which impose the movements sensed by the inductive effect between the corresponding ball 46 and the electrodes 18,20,22 (X,Y,Z coordinates) respectively. The initial conditions of the sensing apparatus (the position of the electrodes and postion of the balls 46) are imposed by the described positioning of the balls 88 and the support systems for the elctrodes 126,128 and 130. The members 62 and 66 with the impressions allow the spacial positioning of the mould which are then fixed by conventional systems to the discs 142 and 148.

The system described enables entirely spontaneous movements, and therefore correct movements, to be determined.

What is claimed is:

1. A system for simulating the condyle movements, comprising a sensing apparatus and a reproducing apparatus which imposes the mastication movements on two arch moulds as determined by the sensing apparatus, wherein:

said sensing apparatus comprises a structure for fitting to the cranium and thereby to the maxillary arch, a structure engageable with the mandible arch, means for generating a signal representing the relative distance between points of the two structures and the front of the arches, at a distance from the condyles, and two induction means each disposed adjacent to a respective one of the two condyles, each said induction means comprising a group of three flat mutually perpendicular reference electrodes mounted on one of the structures, and a ball mounted on the other structure and cooperating with the electrodes in such a manner that a set of three relative positioning signals is generated by induction between the ball and the individual electrodes during the free movements; and said reproducing apparatus comprises two structures movable relative to each other, a base supporting one of said structures, and three extendable articulated members supporting the other of said structures, two of said members each having an end displaceable in two directions under the control of two of the signals of the two sets of three signals, the third signal controlling the extension of said members.

2. A system as claimed in claim 1, wherein the reproducing apparatus further comprises disc means supported by the two structures for carrying the moulds, and the sensing apparatus further comprises bracket means arranged to engage the two structures of the sensing apparatus, and means for forming the two moulds of the patient, said moulds being placed on the respective discs of the two structures of the reproducing apparatus in a spacial position corresponding to that of the arches in the sensing apparatus, and said bracket means being removed before the two apparatuses begin to move.

3. A system as claimed in claim 1, wherein in the sensing apparatus, the structure for fitting to the cranium comprises two slides, a double-threaded bar for moving said slides, arms carried by the slides, and ear pieces, said ear pieces and said groups of three electrodes being carried by said arms, and the structure engageable with the mandible arch comprising two articulated arms having ends at which the balls are mounted, said arms being displaceable symmetrically, means defining a seat in one of said electrodes, and gauging means including a shank for fitting into said seat and means defining a recess for the respective ball, for defining a zero position.

4. A system as claimed in claim 1 wherein, in the sensing apparatus, the structure for fitting to the cranium rests on the glabella, and is engaged with a temporary prothesis on the maxillary arch.

5. A system as claimed in claim 1, wherein, in the reproducing apparatus, one of said structures is a lower structure, and the other of said structures is an upper structure, and the lower one of the two structures comprises two slides which can be adjusted in position to correspond to the position of the two balls, first and second servo-mechanisms linked to the slides, each of said servo-mechanisms being controlled by one of said signals which represents the vertical condyle displacement signal, two further servo-mechanisms controlled by the other two signals for displacing said first and second servo-mechanisms, and a third servo-mechanism coupled to the front of the two structures and operative to set the relative spacing at the front of the apparatus.

6. A system as claimed in claim 5, wherein the reproducing apparatus further comprises two balls carried by the said slides of the lower structure, two additional slides each carrying a group of three flat electrodes which are adjustable to correspond to the position of the electrodes of the sensing apparatus, each said group cooperating with one of said balls, and means for correcting the orientation of the electrodes, in order to introduce corrections to the masticatory movements.

* * * * *